(12) United States Patent
Juan

(10) Patent No.: US 8,297,414 B2
(45) Date of Patent: Oct. 30, 2012

(54) WIRE QUICK RELEASE DEVICE FOR BRAKE WIRE OF BICYCLE

(75) Inventor: Chih-Chen Juan, Wurih Township, Taichung County (TW)

(73) Assignee: Yongmart Manufacturing Co., Ltd., Wurih Township (TW)

( * ) Notice: Subject to any disclaimer, the term of this patent is extended or adjusted under 35 U.S.C. 154(b) by 572 days.

(21) Appl. No.: 12/510,558

(22) Filed: Jul. 28, 2009

(65) Prior Publication Data

US 2010/0212452 A1 Aug. 26, 2010

(30) Foreign Application Priority Data

Feb. 26, 2009 (TW) .............................. 98202896 U

(51) Int. Cl.
*B62L 1/00* (2006.01)
(52) U.S. Cl. .................. 188/24.11; 188/2 D; 188/24.12; 188/24.21; 24/132 R; 74/502.6
(58) Field of Classification Search ............... 188/24.11, 188/24.12, 24.21, 24.22, 65.1, 65.2, 65.3, 188/2 D, 344
See application file for complete search history.

(56) References Cited

U.S. PATENT DOCUMENTS

| | | | | | |
|---|---|---|---|---|---|
| 3,852,943 | A | * | 12/1974 | Healy | 24/134 R |
| 4,034,828 | A | * | 7/1977 | Rose et al. | 182/5 |
| 4,591,026 | A | * | 5/1986 | Nagano | 188/2 D |
| 4,718,521 | A | * | 1/1988 | Hosokawa | 188/24.19 |
| 5,156,240 | A | * | 10/1992 | Ostrobrod | 188/65.1 |
| 6,298,951 | B1 | * | 10/2001 | Wu | 188/24.12 |
| 6,776,267 | B2 | * | 8/2004 | Tsai | 188/24.19 |
| 7,108,099 | B2 | * | 9/2006 | Ador | 182/5 |
| 7,152,498 | B2 | * | 12/2006 | Shahana et al. | 74/502.6 |
| 8,006,809 | B2 | * | 8/2011 | Tsai | 188/24.19 |
| 8,061,487 | B2 | * | 11/2011 | Tsai | 188/24.12 |
| 8,118,141 | B2 | * | 2/2012 | DuPont | 188/24.22 |
| 2006/0243542 | A1 | * | 11/2006 | Tsai | 188/24.11 |

* cited by examiner

*Primary Examiner* — Robert A Siconolfi
*Assistant Examiner* — Mariano Sy
(74) *Attorney, Agent, or Firm* — Apey Juris, pllc; Tracy M Heims

(57) ABSTRACT

A wire quick release device of the present invention is mounted on a bicycle in association with a brake device and a brake wire of the bicycle. The wire quick release device includes a quick release having a handle to operate in order to press the brake wire onto the brake device and loosen the brake wire in order to simplify the work of fastening and releasing the brake wire.

7 Claims, 6 Drawing Sheets

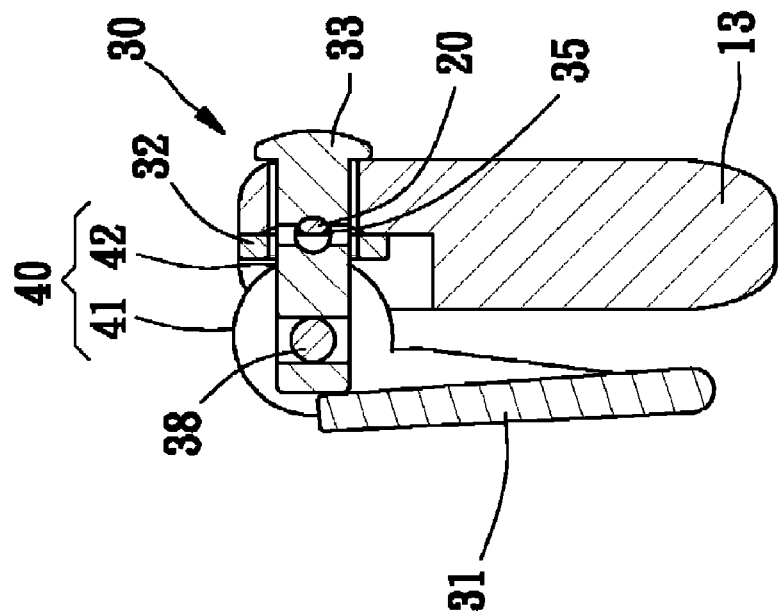
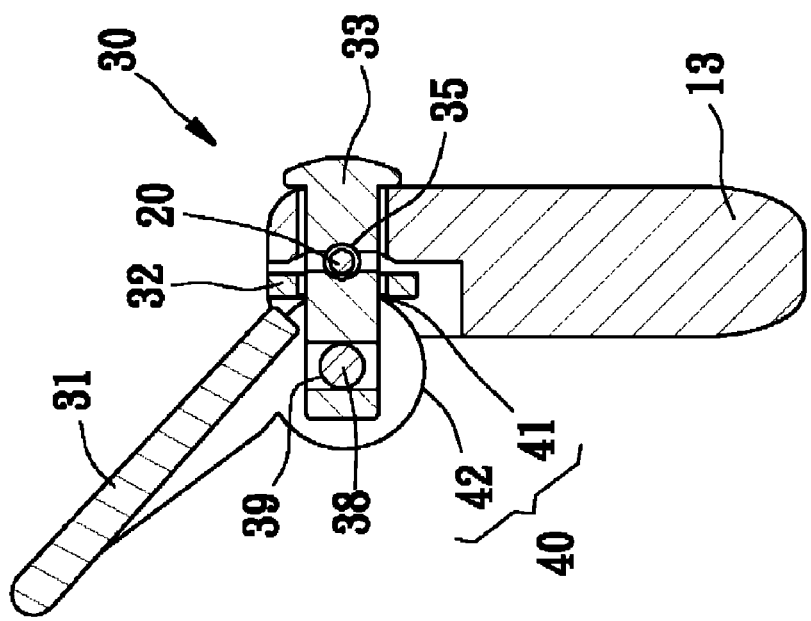
Fig.4
Fig.5

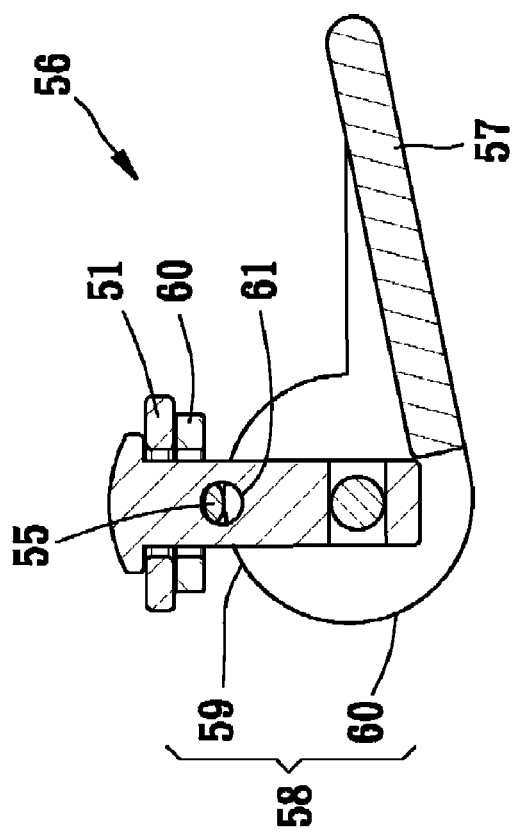
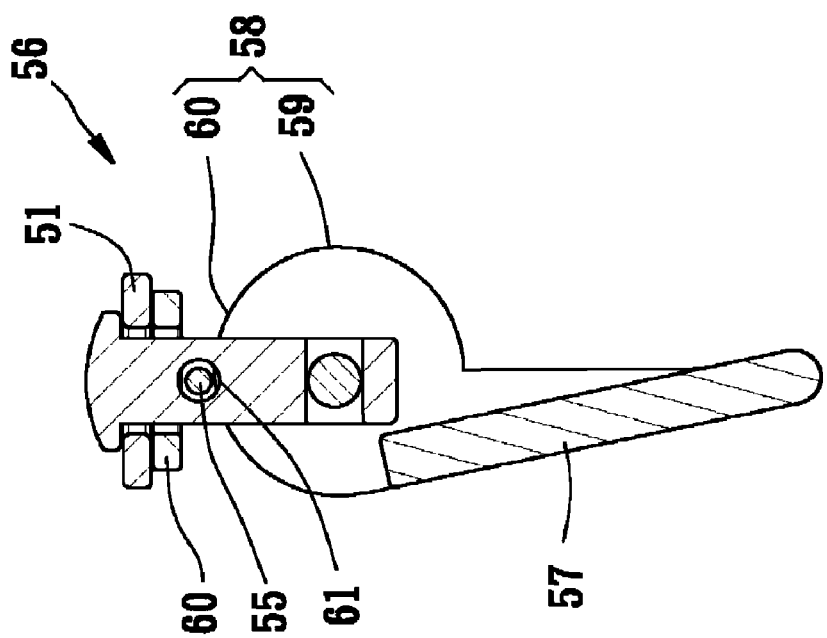
Fig.8
Fig.7

WIRE QUICK RELEASE DEVICE FOR BRAKE WIRE OF BICYCLE

BACKGROUND OF THE INVENTION

1. Field of the Invention

The present invention relates generally to a bicycle, and more particularly to a wire quick release device to fasten and loosen a brake wire of a bicycle.

2. Description of the Related Art

In early days, bicycles were just an economic vehicle for workers and students, until motorcycles and automobiles gradually replaced bicycles and became the main transportation. As health and pollution issues have been commonly concerned in the past decade, nowadays cycling can also be seen in a gym and is considered as a leisure exercise. In 2007 and 2008, the world has a lack of energy supply, and cycling has an advantage of helping with a reduction of carbon dioxide. Now cycling is a popular sport in many cities.

In Taiwan, we have many bikeways designed for bike riders. These specialized bikeways often come with beautiful view and fresh air that riders may enjoy cycling. These bikeways usually are far away from city, so how we transport our bicycles to the destinations becomes a problem.

Except for foldable bicycles, wheels of regular bicycles are able to be taken off so that the frame and the wheels may be put into the back of the truck. To disassemble the wheels, one has to release the quick releases on the forks and loosen the brake wires. For a beginner, figuring out how to loosen the brake wire can be complicated and confusing.

SUMMARY OF THE INVENTION

The primary objective of the present invention is to provide a wire quick release device to quickly fasten and loose a brake wire of a bicycle.

According to the objective of the present invention, a wire quick release device is mounted on a bicycle in association with a brake device and a brake wire of the bicycle. The wire quick release device includes a quick release having a handle to operate in order to press the brake wire onto the brake device and loose the brake wire, which will simplify the work of fastening and releasing the brake wire.

BRIEF DESCRIPTION OF THE DRAWINGS

FIG. 4 is a sectional view along the 4-4 line of FIG. 3, showing the loose condition of the quick release device;

FIG. 5 is a sectional view following FIG. 4, showing the fastened condition of the quick release device;

FIG. 7 is a sectional view of the second preferred embodiment of the present invention, showing the loose condition of the quick release device; and FIG. 8 is a sectional view following FIG. 7, showing the fastened condition of the quick release device.

DETAILED DESCRIPTION OF THE INVENTION

Figure 1:
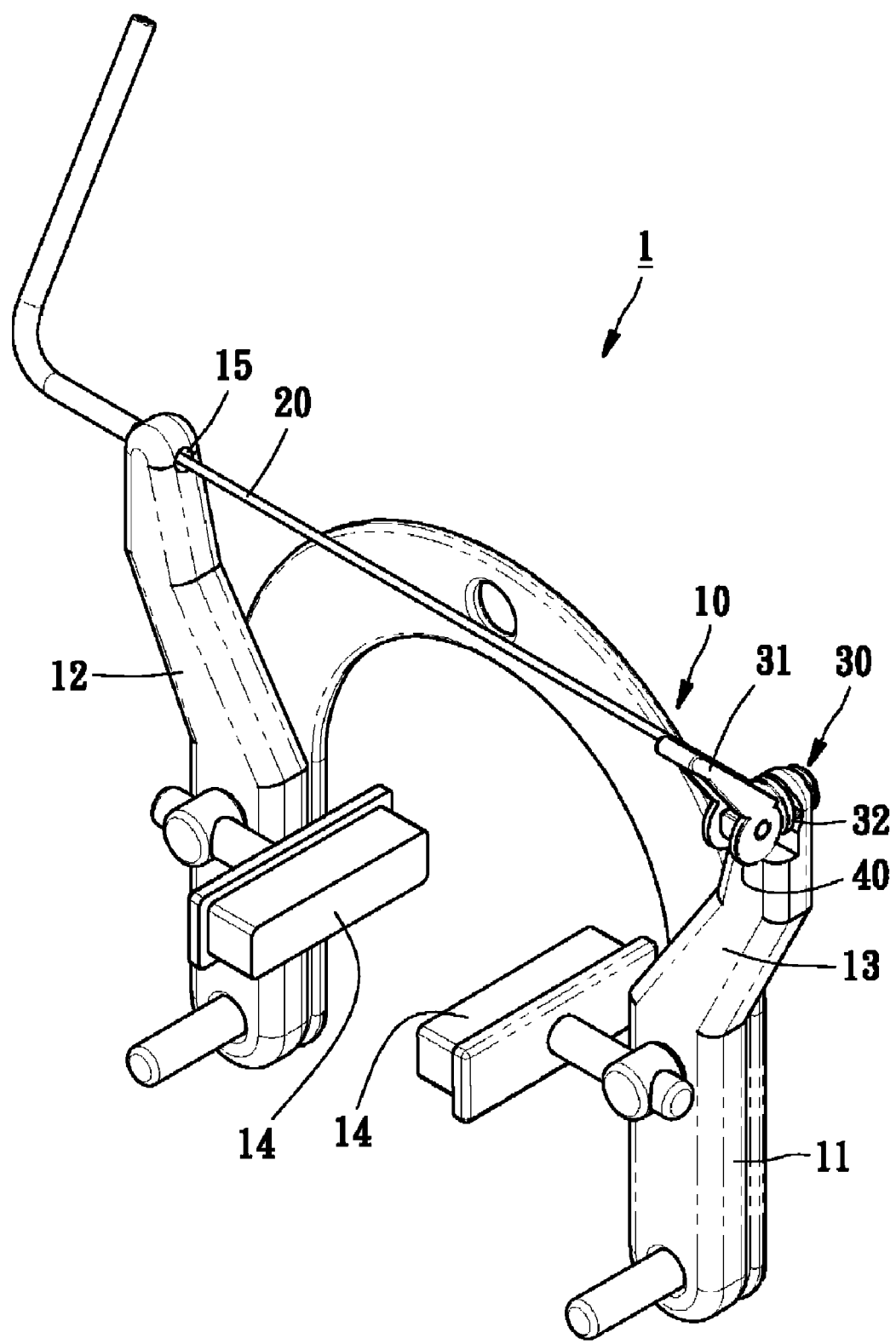
FIG. 1 is a perspective view of a first preferred embodiment of the present invention.
Figure 2:
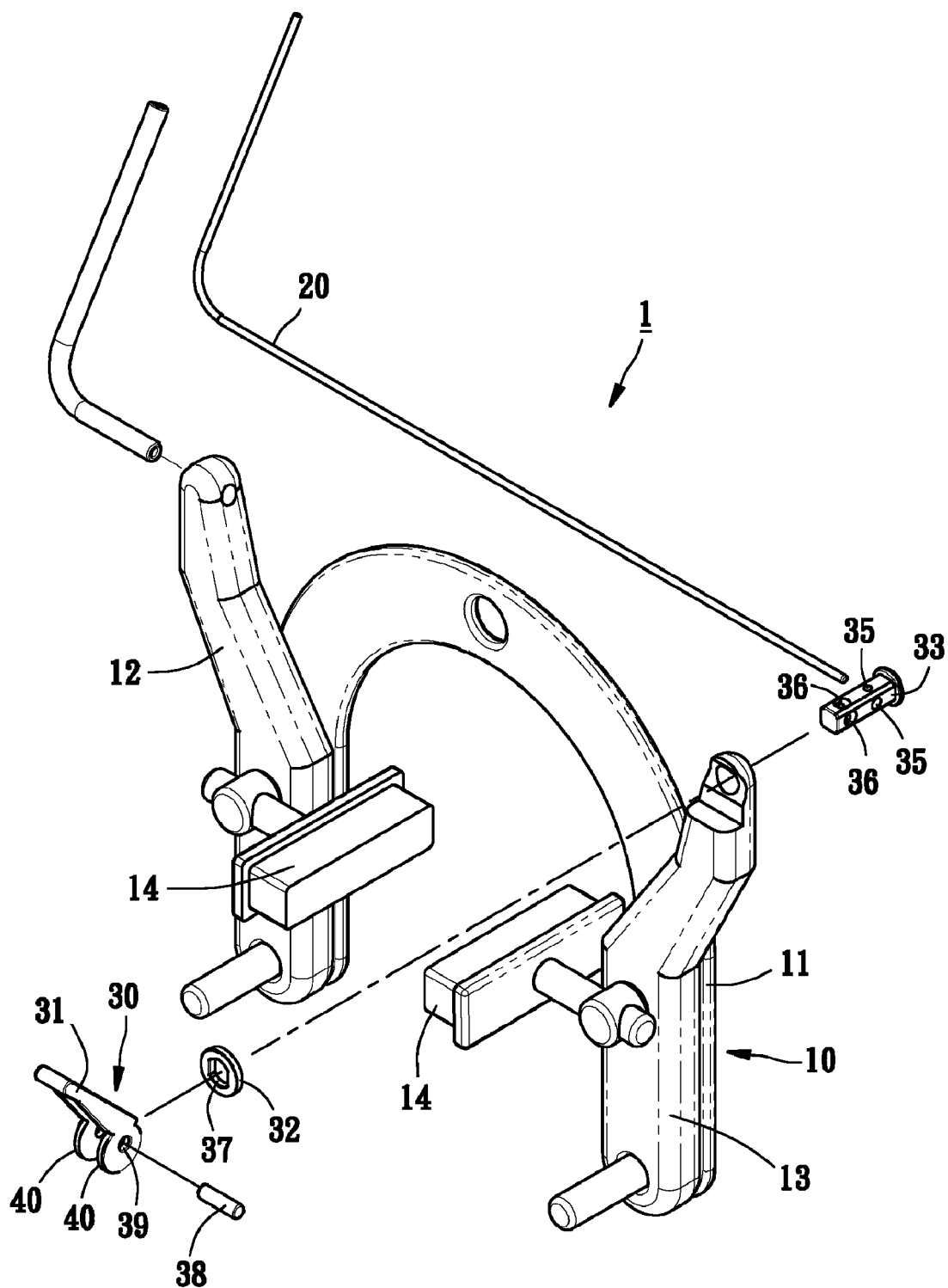
FIG. 2 is an exploded view of the first preferred embodiment of the present invention.
Figure 3:
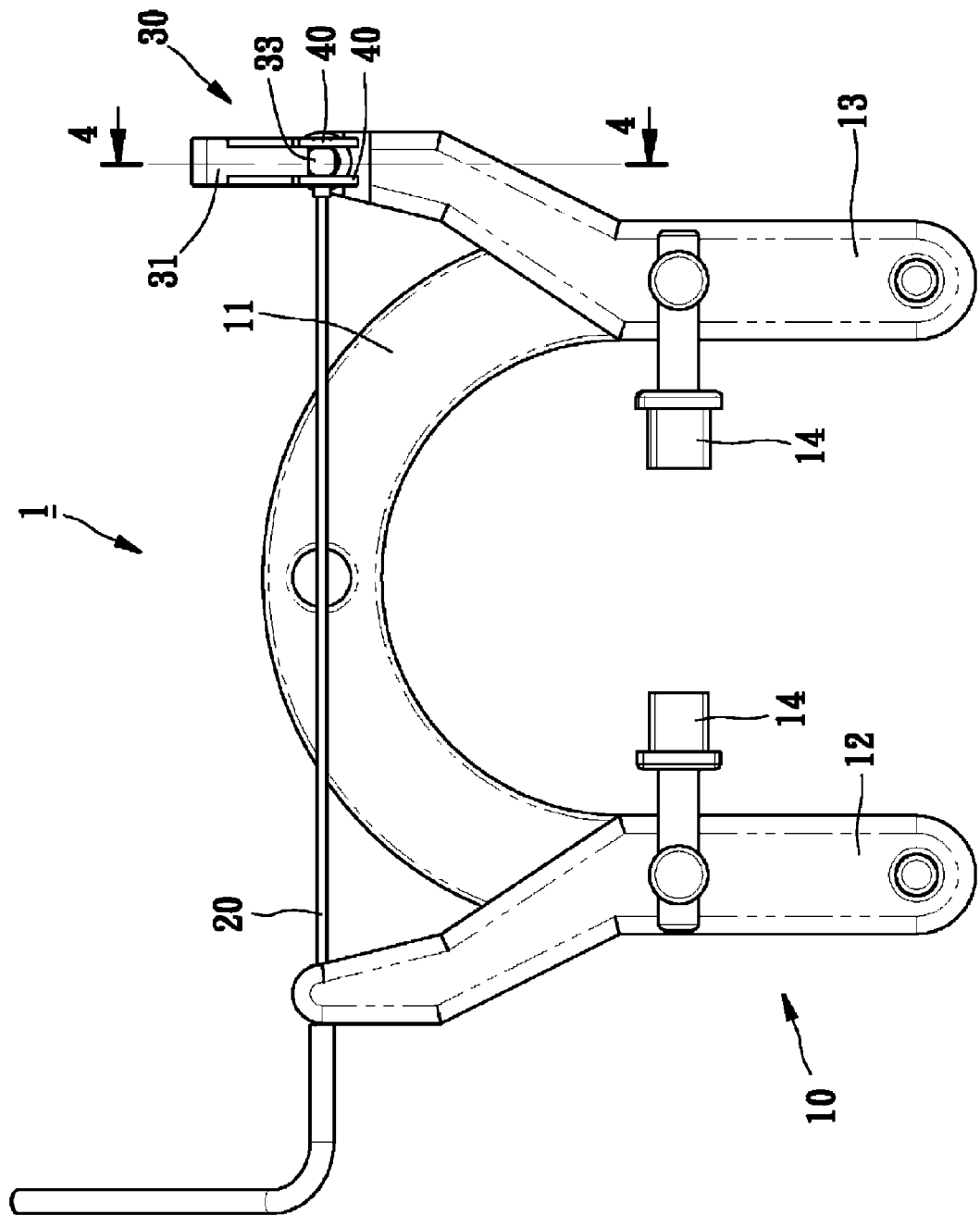
FIG. 3 is a front view of the first preferred embodiment of the present invention.

As shown in FIG. 1 to FIG. 3, a wire quick release device 1 of a bicycle of the first preferred embodiment of the present invention has a brake device 10, a brake wire 20 and a quick release 30.

The brake device 10 has an up-side-down U-shaped base 11, on which two levers 12, 13 are pivoted. Each of the levers 12, 13 is provided with a brake pad 14. The brake wire 20 passes through an opening 15 on the lever 12 and is fastened to the lever 13.

The quick release 30 has a handle 31, a pad 32, and a shaft 33. The shaft 33 is a rectangular shaft having two sets of orthogonal through holes, named first openings 35 and second openings 36. The first openings 35 have different sizes. The shaft 33 passes through an opening 16 of the lever 13. The wire 20 has an end passing through the first opening 35. The pad 32 has a rectangular opening 37 at a center to fit the shaft 33. At last, a pin 38 is inserted into an axial opening 39 of the handle and the second opening 36 of the shaft 33. The handle 31 has a cam portion 40 which has a first section 41 and a second section 42. A distance between the first section 41 and the axial opening 39 is shorter than a distance between the second section 42 and the axial opening 39.

As shown in FIG. 4, when user moves the handle 31 to have the first section 41 touching the pad 32, the quick release 30 is under a loose condition that the brake wire 20 may be inserted into or drawn out of the first opening 35. As shown in FIG. 5, when the handle 31 is moved to have the second section 42 touching the pad 32, the quick release 30 is under a fastened condition that the pad 32 presses the brake wire 20 that the wire 20 is unmovable.

Figure 6:
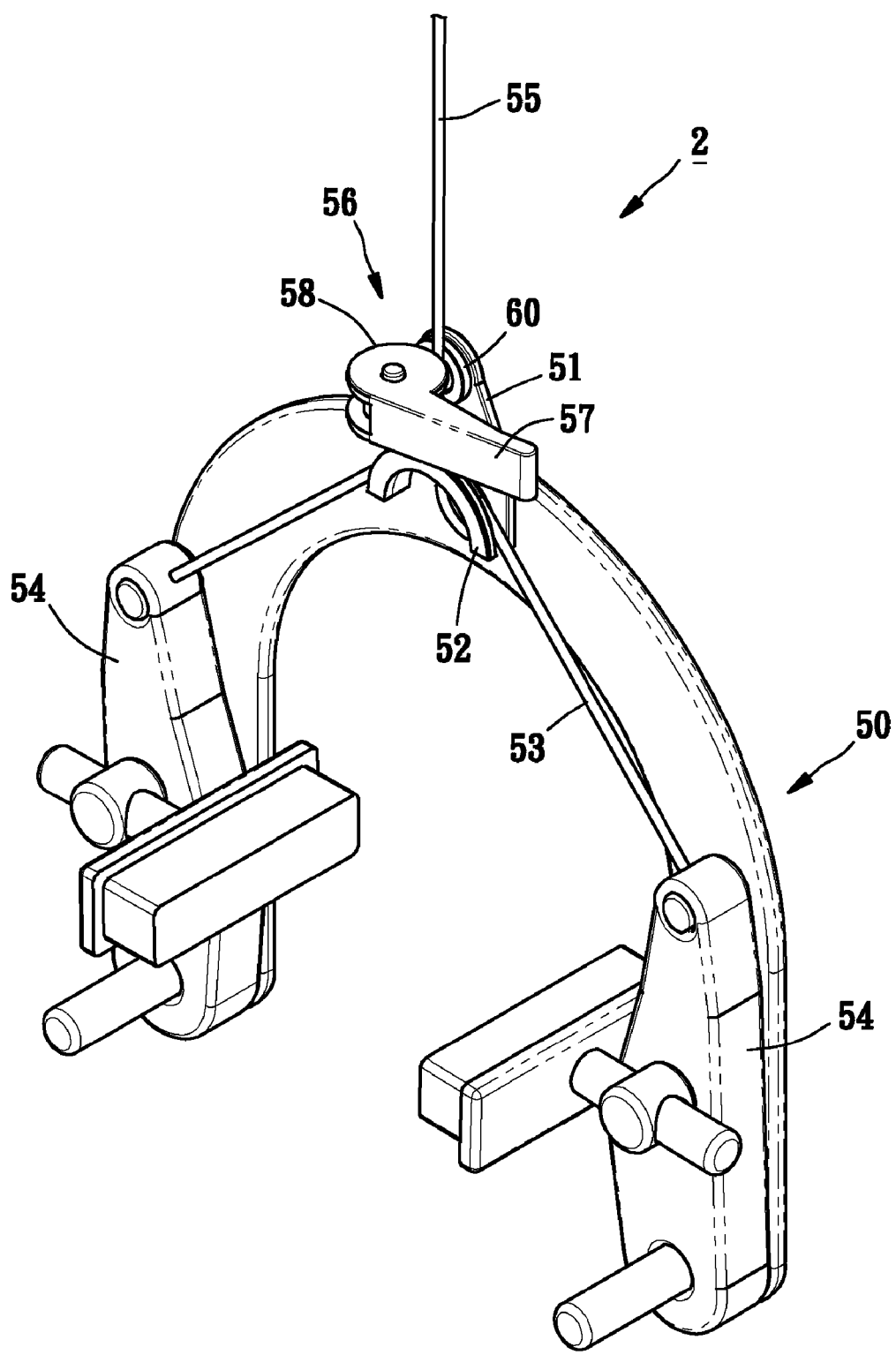
FIG. 6 is a perspective view of a second preferred embodiment of the present invention.

As shown in FIG. 6, a wire quick release device 2 of the second preferred embodiment is similar to the first preferred embodiment, except that a brake device 50 is provided with a movable member 51. The movable member 51 has a curved rail 52. A wire 53 has opposite ends connected to levers 54 respectively. The wire 53 crosses the rail 52 of the movable member 51. A brake wire 55 is connected to the movable member 51 through a quick release 56. As shown in FIG. 7, when a handle 57 of the quick release 56 is moved to have a first section 59 of a cam portion 58 touching a pad 60, the quick release 56 is under a loose condition that the brake wire 55 is able to be moved into or drawn out of a first opening 61. As shown in FIG. 8, when the handle 57 is moved to have a second section 62 of the cam portion 58 touching a pad 60, the quick release 56 is under a fastened condition that the brake wire 55 is pressed by the pad 60 and is unmovable.

The main purpose of the present invention is to simplify the work of fastening and releasing the brake wire and make the work easier and faster via the operation of the quick release.

The description above is a few preferred embodiments of the present invention and the equivalence of the present invention is still in the scope of the claim of the present invention.

What is claimed is:

1. A wire quick release device, which is mounted on a bicycle in association with a brake device and a brake wire of the bicycle, comprising:

a quick release having a handle to operate in order to press the brake wire onto the brake device and loosen the brake wire;

wherein the quick release further includes a shaft, which has an end connected to the brake device, having a first opening for the brake wire to pass through and a second opening, and a pin passing through the second opening of the shaft and an axial opening of the handle.

2. The wire quick release device as defined in claim 1, wherein the handle of the quick release includes the axial opening and a cam portion having a first section and a second section, and further wherein a distance between the first section and the axial opening is shorter than a distance between the second section and the axial opening.

3. The wire quick release device as defined in claim 2, wherein the quick release further includes a pad to be pressed by the second section of the cam portion of the handle.

4. The wire quick release device as defined in claim 1, wherein the shaft has two first openings and two second openings, and the first openings have different sizes.

5. The wire quick release device as defined in claim 1, wherein the shaft is a rectangular shaft having two orthogonal first openings and two orthogonal second openings.

6. The wire quick release device as defined in claim 1, wherein the brake device has two levers, and the quick release is mounted on one of the levers of the brake device, the brake wire passes through an opening of the other lever of the brake device and then is connected to the quick release.

7. The wire quick release device as defined in claim 1, wherein the brake device has two levers,
- a movable member, on which the quick release is mounted, and
- a wire connecting the levers and the movable member; the brake wire is connected to the quick release.

* * * * *